United States Patent [19]

Irick, Jr. et al.

[11] 4,326,065

[45] Apr. 20, 1982

[54] OXADIAZOLE ULTRAVIOLET STABILIZERS AND THEIR USE IN ORGANIC COMPOSITIONS

[75] Inventors: Gether Irick, Jr.; Charles A. Kelly, both of Kingsport, Tenn.

[73] Assignee: Eastman Kodak Company, Rochester, N.Y.

[21] Appl. No.: 159,090

[22] Filed: Jun. 13, 1980

Related U.S. Application Data

[60] Division of Ser. No. 955,449, Oct. 27, 1978, Pat. No. 4,236,013, which is a division of Ser. No. 797,667, Dec. 17, 1976, Pat. No. 4,137,235, which is a continuation of Ser. No. 484,846, Jul. 1, 1974, abandoned.

[51] Int. Cl.$^3$ .......................................... C07D 271/10
[52] U.S. Cl. .................................... 548/143; 548/144
[58] Field of Search ............................... 548/143, 144

[56] References Cited

U.S. PATENT DOCUMENTS 4,116,928  9/1978  Irick, Jr. et al. ............ 260/45.8 NT

OTHER PUBLICATIONS

Gehlen et al., J. Prakt. Chem., vol. 37, pp. 182–191 (1968).
Gehlen et al., Chem. Abstracts, vol. 68, Abstract No. 78203s (1968).
Chemical Abstracts, 8th Coll. Subject Index, p. 21906s (1973).

*Primary Examiner*—Alton D. Rollins
*Attorney, Agent, or Firm*—Clyde L. Tootle; Daniel B. Reece, III

[57] ABSTRACT

The invention relates to heterocyclic ester compounds which have been found to be extremely effective ultraviolet stabilizers. The invention also relates to ultraviolet degradable organic compositions containing an amount of a heterocyclic ester composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions such as polymers by adding to the polymer melt or dissolved in the polymer dope, coated on the exterior of the shaped or molded article, film or extruded fiber.

8 Claims, No Drawings

OXADIAZOLE ULTRAVIOLET STABILIZERS AND THEIR USE IN ORGANIC COMPOSITIONS

This is a division of Ser. No. 955,449, filed Oct. 27, 1978, now U.S. Pat. No. 4,236,013, issued Nov. 25, 1980 which is a division of Ser. No. 797,667, filed Dec. 17, 1976, now U.S. Pat. No. 4,137,235, issued Jan. 30, 1979 which is a continuation of Ser. No. 484,846, filed July 1, 1974, now abandoned.

This invention relates to ultraviolet stabilizers and their use in organic compositions. More particularly, the invention relates to heterocyclic ester compositions and the stabilization of organic compositions against deterioration resulting from the exposure to light with such heterocyclic ester compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb electromagnetic radiation within the band of 2900 to 4000 A. and when incorporated in various plastic materials such as transparent sheets, the resultant sheet acts as a filter for all of the radiation passing through and will transmit only such radiations as are not absorbed by the sheet and/or the absorbing agent. It is thus possible to screen out undesirable radiations and utilize the resulting transparent sheet as a filter in many technical and commercial applications such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is therefore an object of the present invention to provide compositions characterized by improved resistance to degradation and deterioration by ultraviolet radiation.

It is still another object of the present invention to provide compositions containing heterocyclic ester compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations including short wave-length visible radiations.

Further objects and advantages of the invention will be apparent to those skilled in the art from the accompanying disclosure and claims.

In accordance with the present invention, organic compositions are provided which are useful as ultraviolet stabilizers. These organic compositions contain a heterocyclic group connected through a carboxyl group to an aromatic ring which upon exposure to ultraviolet light may undergo the "photo-Fries" rearrangement. The organic compositions of the present invention are aryl esters of heterocyclic aromatic acids having the following structure:

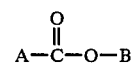

wherein A is a heterocyclic member selected from the group consisting of substituted and unsubstituted 1,3,4-oxadiazole, 1,3,4-thiadiazole, 1,3,4-triazole, benzoxazole, benzothiazole, benzimidazole, thiazole, oxazole, imidazole, and indole, and the like.

Such suitable A components are, for example, members having the formulae:

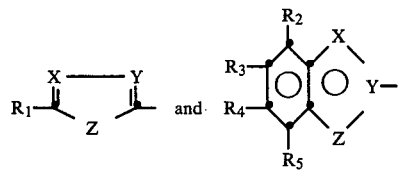

wherein

X and Y are a carbon atom or a nitrogen atom;

Z is an oxygen atom, a sulfur atom, a nitrogen atom, or a nitrogen atom containing a hydrogen atom or a substituted or unsubstituted lower alkyl group having 1 to 12 carbon atoms;

$R_1$, $R_2$, $R_3$, $R_4$ and $R_5$ are hydrogen, lower alkyl, substituted lower alkyl, cycloalkyl, substituted cycloalkyl, aryl, substituted aryl, lower alkylaryl, aryl-substituted-aryl, chloro, bromo, alkoxy, alkylsulfonyl, substituted amino, cyano, nitrile, and the substituents $R_2$, $R_3$, $R_4$ and $R_5$, combined with the carbon atoms to which they are attached, are joined alkylene groups completing a carbocyclic ring which ring can be substituted with any of the substituents listed above for $R_1$ through $R_5$.

Suitable A groups having the formula

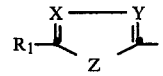

are, for example, substituted and unsubstituted 2-oxadiazolyl, 2-thiazolyl, 2-triazolyl, 2-oxazolyl, and 2-imidazolyl and the like.

Examples of suitable 2-oxadiazolyl moieties are those having the formula:

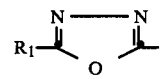

such as 5-(4-chlorophenyl)-1,3,4-oxadiazol-2-yl, 5-phenyl-1,3,4-oxadiazol-2-yl, 5-methylsulfonyl-1,3,4-oxadiazol-2-yl, 5-(2,4-dichlorophenyl)-1,3,4-oxadiazol-2-yl, 5-methyl-1,3,4-oxadiazol-2-yl, 5-(4-phenyl)phenyl-1,3,4-oxadiazol-2-yl, 5-cyano-1,3,4-oxadiazol-2-yl, 5-(4-cyanophenyl)-1,3,4-oxadiazol-2-yl, and 5-(4-methoxyphenyl)-1,3,4-oxadiazol-2-yl, and the like.

Examples of suitable 2-thiadiazolyl moieties are those having the formula:

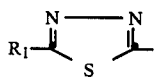

such as 5-phenyl-1,3,4-thiadiazol-2-yl, 5-(4-chlorophenyl)-1,3,4-thiadiazol-2-yl, 5-methylsulfonyl-1,3,4-thiadiazol-2-yl, 5-ethoxy-1,3,4-thiadiazol-2-yl, 5-phenyl-1,3,4-thiadiazol-2-yl, 4-(4-phenyl)phenyl-1,3,4-thiadiazol-2-yl, 4-cyclohexyl-1,3,4-thiadiazol-2-yl, 5-(3-methoxyphenyl)-1,3,4-thiadiazol-2-yl, and 5-cyano-1,3,4-thiadiazol-2-yl, and the like.

Examples of suitable 2-triazolyl moieties are those having the formula:

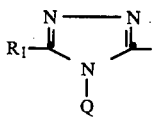

wherein Q is hydrogen or a substituted or unsubstituted lower alkyl group containing 1 to 12 carbon atoms, such as 5-phenyl-1,3,4-triazol-2-yl, 5-(4-cyanophenyl)-1,3,4-triazol-2-yl, 5-cyano-1,3,4-triazol-2-yl, 4-(4-methoxyphenyl)-1,3,4-triazol-2-yl, 1-(n-butyl)-5-(2,4-dichlorophenyl)-1,3,4-triazol-2-yl, 1,3,4-triazol-2-yl, 1H-5-phenyl-1,3,4-triazol-2-yl, 1H-5-methylsulfonyl-1,3,4-triazol-2-yl, 1-methyl-5-phenyl-1,3,4-triazol-2-yl, and the like.

Examples of suitable 2-oxazolyl moieties are those having the formula:

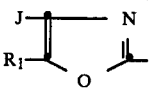

wherein J is the same as $R_1$, such as 5-phenyl-2-oxazolyl, 4,5-diphenyl-2-oxazolyl, 4,5-dimethyl-2-oxazolyl, 4-chloro-5-cyano-2-oxazolyl, 4-phenyl-5-cyano-2-oxazolyl, 5-methylsulfonyl-2-oxazolyl, 5-cyclohexyl-2-oxazolyl, 4,5-dichloro-2-oxazolyl, 5-ethoxy-2-oxazolyl, and the like.

Examples of suitable 2-thiazolyl moieties are those having the formula:

wherein J is the same as $R_1$, such as 4-phenyl-5-chloro-2-thiazolyl, 4,5-dichloro-2-thiazolyl, 4-chloro-5-cyano-2-thiazolyl, 4-ethoxy-5-phenyl-2-thiazolyl, 4,5-dimethyl-2-thiazolyl, 4,5-dicyano-2-thiazolyl, 5-phenyl-2-thiazolyl, and the like.

Examples of suitable 2-imidazolyl moieties are those having the formula:

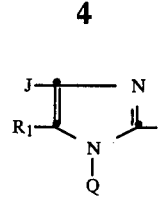

wherein J is the same and $R_1$ and Q is hydrogen or a substituted or unsubstituted lower alkyl having 1 to 12 carbon atoms, such as 1-methyl-4,5-diphenyl-2-imidazolyl, 4-chloro-5-cyano-2-imidazolyl, 5-phenyl-2-imidazolyl, 1-ethyl-5-phenyl-2-imidazolyl, 4,5-diphenyl-2-imidazolyl, 1-benzyl-4-phenyl-5-cyano-2-imidazolyl, 1-methyl-4-cyano-2-imidazolyl, 4-methoxy-5-phenyl-2-imidazolyl, 4,5-dichloro-1-benzyl-2-imidazolyl, and the like.

Suitable A groups having the formula

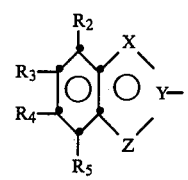

are, for example, substituted and unsubstituted 2-benzoxazolyl, 2-benzothiazolyl, 2-benzimidazolyl and 2-imidolyl.

Examples of suitable 2-benzoxazolyl moieties are those having the formula

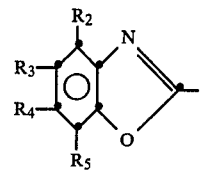

such as 5,6-dimethyl-2-benzoxazolyl, 2-benzoxazolyl, 5-chloro-2-benzoxazolyl, 5,6-dichloro-2-benzoxazolyl, 4,5-diethyl-2-benzoxazolyl, 5-cyano-2-benzoxazolyl, 5-methoxy-6-methyl-2-benzoxazolyl, 4-chloro-5-phenyl-2-benzoxazolyl, and the like.

Examples of suitable 2-benzothiazolyl moieties are those having the formula

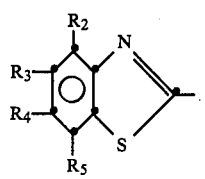

such as 2-benzothiazolyl, 5,6-dimethyl-2-benzothiazolyl, 5,6-dichloro-2-benzothiazolyl, 5-chloro-2-benzothiazolyl, 5-methoxy-2-benzothiazolyl, 6-methylsulfonyl-2-benzothiazolyl, 6-cyano-2-benzothiazolyl, 6-methylthio-2-benzothiazolyl, and 6-methyl-2-benzothiazolyl.

Examples of suitable 2-benzimidazolyl moieties are those having the formula

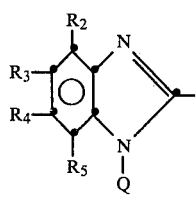

wherein Q is hydrogen or a substituted or unsubstituted lower alkyl containing 1 to 12 carbon atoms, such as 2-benzimidazolyl, 1-methyl-2-benzimidazolyl, 1,5,6-trimethyl-2-benzimidazolyl, 6-cyano-1-ethyl-2-benzimidazolyl, 6-chloro-2-benzimidazolyl, 5-methoxy-1-benzyl-2-benzimidazolyl, 6-methylsulfonyl-2-benzimidazolyl, 4-methoxy-1-methyl-2-benzimidazolyl, and the like.

Examples of suitable indole moieties are those having the formula

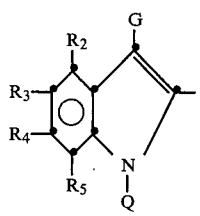

wherein G is the same as $R_1$, and Q is hydrogen or a substituted or unsubstituted lower alkyl containing 1 to 12 carbon atoms. Such suitable indole moieties are, for example, 1-ethyl-3-cyano-2-indolyl, 5-chloro-2-indolyl, 1-methyl-2-indolyl, 3-methyl-2-indolyl, 3-chloro-2-indolyl, 5-acetamido-2-indolyl, 2-indolyl, 1-ethyl-2-indolyl, 3-cyano-2-indolyl, 5-methoxy-2-indolyl, 1-methyl-2-indolyl, 3-methyl-5-phenyl-2-indolyl and 3,5-dichloro-2-indolyl.

Suitable B groups having the formula

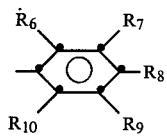

are 2,4-dimethoxyphenyl, 3-methoxyphenyl, 3-methylphenyl, 4-octylphenyl, 4-dodecylphenyl, 3-octylphenyl, 2,4-dichlorophenyl, 4-methoxyphenyl, 2,4-di-t-butylphenyl, 3-(2-ethylhexyloxy)phenyl, 3-dodecyloxyphenyl, 4-cyanophenyl, 4-bromophenyl, 3-hydroxyphenyl and 3-cyclohexylphenyl.

"Lower alkyl" as used in this application means branched or unbranched, substituted or unsubstituted alkyl groups containing 1 to 12 carbon atoms. The substituents on the lower alkyl groups can be any of those listed hereinabove for $R_1$. "Alkyl" as used herein means branched or unbranched, substituted or unsubstituted alkyl groups containing 1 to 20 carbon atoms which are substituted with the same substituents as $R_1$. Substituted aryl and cycloalkyl groups are also substituted by the same substituents as $R_1$. The "alk" of alkoxy and carboalkoxy means an alkyl radical containing 1 to 20 carbon atoms.

The heterocyclic esters can be prepared by reacting the acid chloride with a phenol. For example, one such group of organic compounds useful as ultraviolet stabilizers is, for example, benzoxazole ester-based compositions having the formula

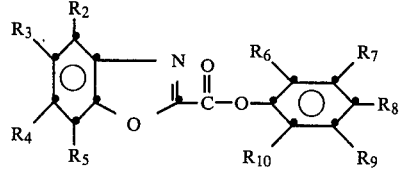

These organic compounds can be prepared according to the following procedure:

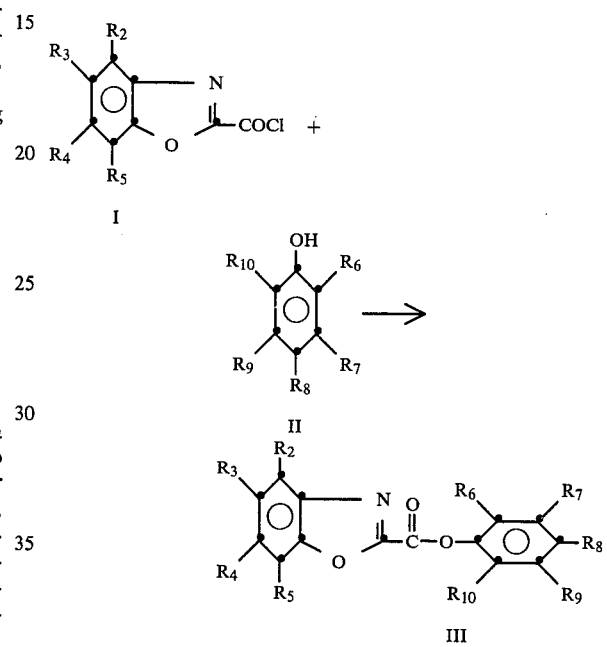

Substituents $R_2$ through $R_{10}$ are defined hereinabove. It is necessary that at least one of $R_6$ or $R_{10}$ be hydrogen so that, on exposure to ultraviolet light, the aryl ester of the heterocyclic aromatic acid is capable by the "photo-Fries" rearrangement of forming a phenol group in that position formerly joined through an oxygen atom to the carbonyl linking group, as for example

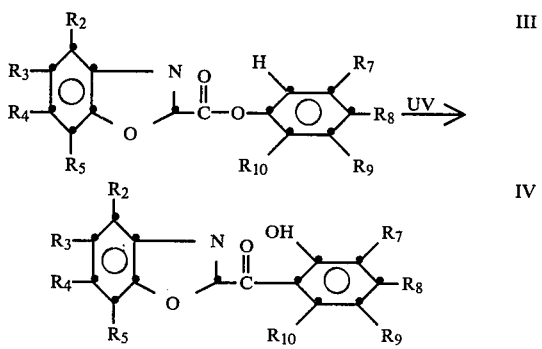

The acid chlorides (I) were prepared by reaction of the corresponding acid [See *Zh. Obshch. Khim.*, 38, 100 1-5 (1968); *Chem. Abstr.* 69, 96568 (1968)] with freshly distilled thionyl chloride [See *J. Chem. Soc.* 101, 2476 (1912)]. The phenols were obtained from commercial sources, or were prepared by standard methods; a critical requirement is that one of the positions adjacent to the phenolic hydroxyl group be unsubstituted. It is believed that the "photo-Fries" rearrangement can occur upon ultraviolet exposure of the esters III and that these rearrangement products IV are effective stabilizers.

The heterocyclic ester compositions can be added to organic compositions which are susceptible to ultraviolet degradation. Such compositions include, for example, polymeric compositions such as polyester fiber and moldable compositions, such as poly(ethylene terephthalate), poly(tetramethylene terephthalate) and the like; unsaturated polyesters; polyolefins such as, for example, high, medium and low density polyethylene, polypropylene, polybutene and the like; polyamides such as nylon 6, nylon 66 and the like; polycarbonates; poly(vinyl chloride); cellulose esters; cellulose ethers; acrylic/butadiene/styrene plastic; acrylics such as polymethyl methacrylate; polystyrene; and gelatin. Such compositions also include natural and synthetic rubbers such as polybutadiene, and unsaturated organic compositions such as oils and the like, as well as compositions containing such organic compositions.

The heterocyclic ester compositions as effective ultraviolet stabilizers or screening agents are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 5%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These heterocyclic ester ultraviolet stabilizers may be incorporated into organic compositions by melt-blending or may be added onto the surface of an organic plastic material prior to being molded into a suitable object, or added to the surface of the molded object. These materials can also be added to coatings and the like which can be applied to the surface of a molded object.

This invention will be further illustrated by the following examples, although it will be understood that these examples are included merely for purposes of illustration and are not intended to limit the scope of the invention.

EXAMPLE 1

4-(1,1,3,3-Tetramethylbutyl)phenyl 4-chloro-5-phenyloxazole-2-carboxylate can be prepared by the following procedure:

To a solution of 4.0 g. (0.1 mole) of sodium hydroxide in 200 ml. of water was added 20.6 g. (0.1 mole) of 4-(1,1,3,3-tetramethylbutyl)phenol. The mixture was stirred for 10 minutes and 200 ml. of chloroform was added, followed by the dropwise addition of a solution of 24.2 g. (0.1 mole) 4-chloro-5-phenyl-2-oxazolecarbonyl chloride in 500 ml. of chloroform. The mixture was stirred at reflux for 3 hours after the addition was complete. The reaction mixture was cooled to 30° C. and the chloroform layer separated and washed with water. The solvent was removed by distillation, the residue triturated with 100 ml. chilled isopropyl alcohol, and the crude product collected by filtration. The tan solid was recrystallized from toluene to give 26 g. of white solid.

Other oxazole esters can be prepared by substituting other oxazolecarbonyl chlorides, such as 4,5-dimethyl-2-oxazolecarbonyl chloride, 4-chloro-5-cyano-2-oxazolecarbonyl chloride, 4,5-diphenyl-2-oxazolecarbonyl chloride, 4-phenyl-5-cyano-2-oxazolecarbonyl chloride, 5-methylsulfonyl-2-oxazolecarbonyl chloride, 5-cyclohexyl-2-oxazolecarbonyl chloride, 4,5-dichloro-2-oxazolecarbonyl chloride, 5-ethoxy-2-oxazolecarbonyl chloride, 5,6-dimethyl-2-benzoxazolecarbonyl chloride, 2-benzoxazolecarbonyl chloride, 5-chloro-2-benzoxazolecarbonyl chloride, 5,6-dichloro-2-benzoxazolecarbonyl chloride, 5,6-diethyl-2-benzoxazolecarbonyl chloride, 5-cyano-2-benzoxazolecarbonyl chloride, 5-methoxy-6-methyl-2-benzoxazolecarbonyl chloride, for 4-chloro-5-phenyl-2-oxazolecarbonyl chloride.

Also, other oxazole esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for 4-(1,1,3,3-tetramethylbutyl)phenol.

EXAMPLE 2

3-Methylphenyl 4,5-diphenylthiazole-2-carboxylate can be similarly prepared by the procedure of Example 1 as follows:

10.8 g. m-cresol (0.1 mole) was added to a solution of 4.0 g. (0.1 mole) sodium hydroxide in 200 ml. of water. A solution of 30 g. of 4,5-diphenyl-2-thiazolecarbonyl chloride was added and refluxing continued for 3 hours. On workup, 31 g. of a white solid was obtained.

Other thiazole esters can be prepared by substituting other thiazolecarbonyl chlorides, such as 4-phenyl-5-chloro-2-thiazolecarbonyl chloride, 4,5-dichloro-2-thiazolecarbonyl chloride, 4-chloro-5-cyano-2-thiazolecarbonyl chloride, 4-ethoxy-5-phenyl-2-thiazolecarbonyl chloride, 4,5-dimethyl-2-thiazolecarbonyl chloride, 4,5-dicyano-2-thiazolecarbonyl chloride, 5-phenyl-2-thiazolecarbonyl chloride, 2-benzothiazolecarbonyl chloride, 5,6-dimethyl-2-benzothiazolecarbonyl chloride, 5,6-dichloro-2-benzothiazolecarbonyl chloride, 5-chloro-2-benzothiazolecarbonyl chloride, 5-methoxy-2-benzothiazolecarbonyl chloride, 6-methylsulfonyl-2-benzothiazolecarbonyl chloride, 6-cyano-2-benzothiazolecarbonyl chloride, 6-methylthio-2-benzothiazolecarbonyl chloride and 6-methyl-2-benzothiazolecarbonyl chloride for 4,5-diphenylthiazole-2-carboxylic acid chloride.

Also, other thiazole esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for m-cresol.

EXAMPLE 3

4-Dodecyloxyphenyl 1-methyl-5-phenylimidazole-2-carboxylate can similarly be prepared by the procedure of Example 1 by reacting p-dodecyloxyphenol (27.8 g.) with 22 g. 1-methyl-5-phenylimidazole-2-carbonyl chloride to provide 41 g. light tan product.

Other imidazoles can be prepared by substituting 5-phenylimidazole-2-carbonyl chloride, 1-ethyl-5-phenylimidazole-2-carbonyl chloride, 4,5-diphenylimidazole-2-carbonyl chloride, 1-benzyl-4-phenyl-5-cyanoimidazole-2-carbonyl chloride, 1-methyl-4-cyanoimidazole-2-carbonyl chloride, 4-methoxy-5-phenylimidazole-2-carbonyl chloride, 4,5-dichloro-1-benzylimidazole-2-carbonyl chloride, benzimidazole-2-carbonyl chloride, 1-methylbenzimidazole-2-carbonyl chloride, 1,5,6-trimethylbenzimidazole-2-carbonyl chloride, 6-cyano-1-ethylbenzimidazole-2-carbonyl chloride, 6-chlorobenzimidazole-2-carbonyl chloride, 5-methoxy-1-benzylbenzimidazole-2-carbonyl chloride, 6-methylsulfonylbenzimidazole-2-carbonyl chloride, 4-methoxy-1-methylbenzimidazole-2-carbonyl chloride, for 1-methyl-5-phenylimidazole-2-carbonyl chloride.

Also, other imidazole esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 4-methoxyphenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 2,4-di-t-butylphenol, for p-dodecyloxyphenol.

EXAMPLE 4

3-Methoxyphenyl 5-phenyl-1,3,4-oxadiazole-2-carboxylate can be prepared by the procedure of Example 1 by reacting 3-methoxyphenol (12.4 g.) with 21 g. 5-phenyl-1,3,4-oxadiazole-2-carbonyl chloride to provide 24 g. colorless product.

Other oxadiazole esters can be prepared by substituting 5-methyl-1,3,4-oxadiazole-2-carbonyl chloride, 5-(4-phenyl)phenyl-1,3,4-oxadiazole-2-carbonyl chloride, 5-cyano-1,3,4-oxadiazole-2-carbonyl chloride, 5-(4-cyanophenyl)-1,3,4-oxadiazole-2-carbonyl chloride, and 5-(4-methoxyphenyl)-1,3,4-oxadiazole-2-carbonyl chloride, 1,3,4-oxadiazole-2-carbonyl chloride, 5-chloro-1,3,4-oxadiazole-2-carbonyl chloride, 5-chloromethyl-1,3,4-oxadiazole-2-carbonyl chloride, 5-dimethylamino-1,3,4-oxadiazole-2-carbonyl chloride for 5-phenyl-1,3,4-oxadiazole-2-carbonyl chloride.

Also, other oxadiazole esters can be prepared by substituting other phenols, such as 2,4-dimethoxyphenol, 3-methylphenol, 4-octylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4di-t-butylphenol, 4-methylphenol, 3-chlorophenol, 3,5-dimethyl-4-cyanophenol for 3-methoxyphenol.

EXAMPLE 5

4-Chlorophenyl 5-cyano-1,3,4-thiadiazole-2-carboxylate can be prepared by reacting 4-chlorophenol (12.9 g.) with 17.4 g. 5-cyano-1,3,4-thiadiazole-2-carbonyl chloride as in Example 1 to give 22 g. light tan product.

Other thiadiazole esters can be prepared by substituting 5-ethoxy-1,3,4-thiadiazole-2-carbonyl chloride, 5-phenyl-1,3,4-thiadiazole-2-carbonyl chloride, 5-(4-phenyl)phenyl-1,3,4-thiadiazole-2-carbonyl chloride, 5-cyclohexyl-1,3,4-thiadiazole-2-carbonyl chloride, and 5-(3-methoxyphenyl)-1,3,4-thiadiazole-2-carbonyl chloride for 5-cyano-1,3,4-thiadiazole-2-carbonyl chloride.

Also, other thiadiazole esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 3-bromophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 4-methoxyphenol, 2,4-di-t-butylphenol, for 4-chlorophenol.

EXAMPLE 6

3-Octyloxyphenyl 1,3,4-triazole-2-carboxylate can be prepared by reacting 3-octyloxyphenol (22.2 g.) with 13 g. 1,3,4-triazole-2-carbonyl chloride as in Example 1 to yield 14 g. colorless product.

Other triazole esters can be prepared by substituting 5-phenyl-1,3,4-triazole-2-carbonyl chloride, 5-(4-cyanophenyl)-1,3,4-triazole-2-carbonyl chloride, 5-cyano-1,3,4-triazole-2-carbonyl chloride, 5-(4-methoxyphenyl)-1,3,4-triazole-2-carbonyl chloride, and 1-(n-butyl)-5-(2,4-dichlorophenyl)-1,3,4-triazole-2-carbonyl chloride for 1,3,4-triazole-2-carbonyl chloride.

Also, othe triazole esters can be prepared by substituting other phenols, such as 2,4-dimethoxyphenol, 3-methoxyphenol, 3-methylphenol, 4-octylphenol, 4-dodecylphenol, 3-octylphenol, 2,4-dichlorophenol, 4-methoxyphenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-dimethylphenol, 2,4-di-t-butylphenol, for 3-octyloxyphenol.

EXAMPLE 7

3-Methoxyphenyl 1-methylindole-2-carboxylate can be prepared by the procedure of Example 1 by reacting 3-methoxyphenol (12.4 g.) with 19 g. 1-methylindole-2-carbonyl chloride to provide 22 g. light tan product.

Other indole esters can be prepared by substituting 1-benzyl-3-chloroindole-2-carbonyl chloride, 3-cyanoindole-2-carbonyl chloride, 1,3,5-trimethylindole-2-carbonyl chloride, 1-ethyl-3-cyanoindole-2-carbonyl chloride, 1-methyl-3-phenyl-5-chloroindole-2-carbonyl chloride for 1-methylindole-2-carbonyl chloride.

EXAMPLE 8

The stabilizing effects of the ultraviolet stabilizers of the present invention in polyester plastic are shown in the following table:

| Weathering Results for Stabilizers in Poly(tetramethylene terephthalate) Plastic | | | |
|---|---|---|---|
| Additive Compound | FWIS[b] | | |
| (at 1%)[a] | 0 | 300 | 500 |
| Example 1 | 18 | 18 | 18 |
| 2 | 19 | 18 | 12 |
| 3 | 19 | 18 | 16 |
| 4 | 19 | 18 | 14 |
| 5 | 19 | 18 | 13 |
| 6 | 18 | 18 | 16 |
| 7 | 19 | 18 | 18 |
| None | 18 | 6 | 1 |

[a]Incorporated into the polyester (1.50 I.V.) by dry-blending the powdered components, extrusion into 1/16″ diameter rod and injection molding into 1/16″ thick flat bars.
[b]Flatwise-Impact-Strength (ft.-lb./in.$^2$) after exposure to mercury lamps for the hours indicated.

These esters of heterocyclic aromatic acid compositions find particular utility as ultraviolet stabilizers in organic compositions requiring ultraviolet stability. Such compositions include polymeric compositions such as, for example, polyester fiber and molding compositions; poly-α-olefins; polyamides; acrylics; cellulose esters and the like, as well as molded or shaped articles, film and coatings formed from such materials, and the like. Such compositions also include natural and synthetic rubbers, such as natural rubber, as well as organic materials such as oils, fats, and unsaturated organic materials, and materials having such materials contained therein, such as paints, varnishes, cosmetics and the like.

The invention has been described in detail with particular reference to preferred embodiments thereof, but it will be understood that variations and modifications can be effected within the spirit and scope of the invention.

We claim:

1. A composition of matter having the formula:

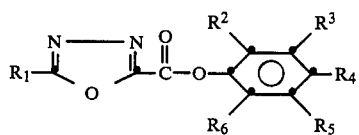

wherein $R_1$ is hydrogen, chloro, bromo, lower alkyl containing 1 to 12 carbon atoms, cyclohexyl, phenyl, lower alkyl phenyl, phenyl-substituted phenyl, alkoxy containing an alkyl radical containing 1 to 20 carbon atoms, chloromethyl and dimethyl amino; at least one $R_2$ or $R_6$ is hydrogen and the other $R_2$, $R_3$, $R_4$, $R_5$ and $R_6$ are hydrogen, lower alkyl having 1 to 12 carbon atoms, cyclohexyl, phenyl, lower alkyl phenyl, phenyl-substituted-phenyl, alkoxy containing an alkyl radical containing 1 to 20 carbon atoms, dimethyl substituted amino, hydroxy, nitrile, chloro and bromo.

2. A composition of matter according to claim 1 having the formula:

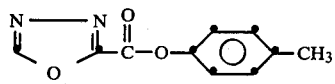

3. A composition of matter according to claim 1 having the formula:

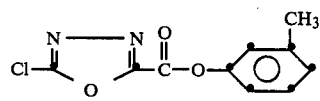

4. A composition of matter according to claim 1 having the formula:

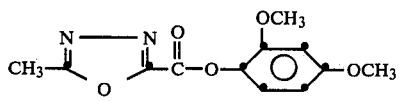

5. A composition of matter according to claim 1 having the formula:

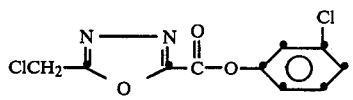

6. A composition of matter according to claim 1 having the formula:

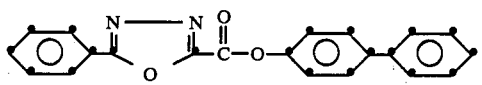

7. A composition of matter according to claim 1 having the formula:

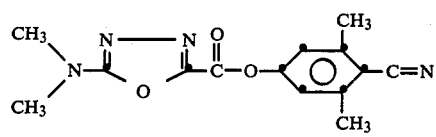

8. A composition of matter according to claim 1 having the formula:

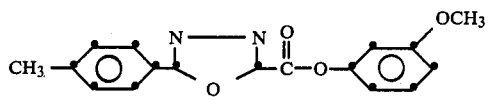

* * * * *

UNITED STATES PATENT AND TRADEMARK OFFICE
CERTIFICATE OF CORRECTION

PATENT NO. : 4,326,065
DATED : April 20, 1982
INVENTOR(S) : Gether Irick, Jr. and Charles A. Kelly It is certified that error appears in the above—identified patent and that said Letters Patent is hereby corrected as shown below:

Column 12, Claim 8, delete the formula and insert therefor:

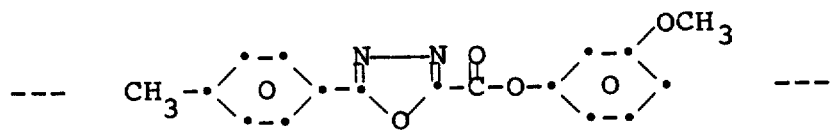

Signed and Sealed this

Seventeenth Day of May 1983

[SEAL]

Attest:

DONALD J. QUIGG

Attesting Officer

Acting Commissioner of Patents and Trademarks